US008546528B2

(12) United States Patent
Janssen et al.

(10) Patent No.: US 8,546,528 B2
(45) Date of Patent: Oct. 1, 2013

(54) SKIN OR HAIR BINDING PEPTIDES

(75) Inventors: Giselle Janssen, San Carlos, CA (US); Christopher J. Murray, Soquel, CA (US); Deborah Winetzky, Foster City, CA (US)

(73) Assignee: Danisco US Inc., Palo Alto, CA (US)

( * ) Notice: Subject to any disclaimer, the term of this patent is extended or adjusted under 35 U.S.C. 154(b) by 987 days.

(21) Appl. No.: 12/534,695

(22) Filed: Aug. 3, 2009

(65) Prior Publication Data

US 2010/0168383 A1   Jul. 1, 2010

Related U.S. Application Data

(63) Continuation of application No. 10/533,701, filed as application No. PCT/US03/36234 on Nov. 12, 2003, now abandoned.

(60) Provisional application No. 60/429,051, filed on Nov. 25, 2002.

(51) Int. Cl.
*A61K 38/04* (2006.01)
*A61K 38/00* (2006.01)
*C07K 5/00* (2006.01)
*C07K 7/00* (2006.01)
*C07K 16/00* (2006.01)
*C07K 17/00* (2006.01)

(52) U.S. Cl.
USPC ........... 530/329; 530/327; 530/344; 530/333; 530/338; 514/1.1

(58) Field of Classification Search
None
See application file for complete search history.

(56) References Cited

U.S. PATENT DOCUMENTS

| | | | | |
|---|---|---|---|---|
| 4,683,202 | A | 7/1987 | Mullis | 435/91 |
| 5,270,181 | A | 12/1993 | McCoy et al. | 435/69.7 |
| 5,283,173 | A | 2/1994 | Fields et al. | 435/6 |
| 5,292,646 | A | 3/1994 | McCoy et al. | 435/69.7 |
| 5,475,096 | A | 12/1995 | Gold et al. | 536/23.1 |
| 5,605,793 | A | 2/1997 | Stemmer | 435/6 |
| 5,733,731 | A | 3/1998 | Schatz et al. | 435/6 |
| 7,220,405 | B2 | 5/2007 | Huang et al. | |
| 7,285,264 | B2 | 10/2007 | O'Brien et al. | |
| 7,309,482 | B2 | 12/2007 | Buseman-Williams et al. | |
| 2003/0152976 | A1 | 8/2003 | Janssen et al. | 435/6 |
| 2008/0107614 | A1 | 5/2008 | Fahnestock et al. | |

FOREIGN PATENT DOCUMENTS

| | | |
|---|---|---|
| WO | WO 96/16630 | 6/1996 |
| WO | WO 96/33010 | 10/1996 |
| WO | WO 97/22617 | 6/1997 |
| WO | WO 98/54312 | 12/1998 |
| WO | WO 00/24372 | 5/2000 |
| WO | WO 01/79479 | 10/2001 |

OTHER PUBLICATIONS

Database Accession No. 429043-49-2; Database Registry (Online) Chemical Abstract, Columbus Ohio; Jun. 12, 2002; XP002587261.
Da Silva, A.C.R., et al., "Comparison of the genomes of two *Xanthomonas* pathogens with differing host specificities." *Nature* 417: 459-463, 2002.
Supplementary European Search Report for European Patent Application No. EP 03 78 9748, dated Jun. 16, 2010.
International Search Report for International Application No. PCT/US03/36234 dated Nov. 8, 2005.
Ausubel et al., *Current Protocols in Molecular Biology*, Greene-Publishing & Wiley Interscience NY (Supplemented through 1999), 1987.
Balass et al., "Recovery of High-Affinity Phage from a Nitrostreptavidin Matrix in Phage-Display Technology, *Analytical Biochemistry*," 243:264-269, 1996.
Barbas, "Recent Advances in Phage Display," *Current Opinion in Biotechnology*, 4:526-530, 1993.
Bartoli, et al., "DNA-based selection and screening of peptide ligands," *Nature Biotechnology*, 16:1068-1074, Nov. 1998.
Berger and Kimmel, *Methods in Enzymology*, vol. 152, (1987) Academic Press, Inc., San Diego, CA.
Cao et al., "Detecting and Identifying Active Compounds from a Combinatorial Library Using IAsys and Electrospray Mass Spectrometry," *Techniques in Protein Chemistry VIII, Ed.* By Marshak, pp. 177-184, 1997.
Cheng et al., "Using Electrospray Ionization FTICR Mass Spectrometry to Study Competitive Binding of Inhibitors to Carbonic Anhydrase," *J. Am. Chem. Soc.*, vol. 117, pp. 8859-8860, 1995.
Christian et al., "Simplified Methods for Construction, Assessment and Rapid Screening of Peptide Libraries in Bacteriophage," *J. Mol. Biol.*, 227:711-718, 1992.
*CTFA International Buyers' Guide*, 2002, Cosmetic, Toiletry and Fragrance Association, Washington, D.C.
Wenninger, John A. et al., ed., CTFA *International Cosmetic Ingredient Dictionary and Handbook*, 7th ed., vol., 2 p. 1672, 1997.
Cull et al., "Screening for receptor ligands using large libraries of peptides linking to the C terminus of the *lac* repressor," *Proc. Natl. Acad. Sci*, USA, vol. 89, pp. 1865-1869, Mar. 1992.
Cwirla et al., "Peptides on phage: A vast library of peptides for identifying ligands," *Proc. Natl. Acad. Sci.* USA, 87:6378-6382, Aug. 1990.
Fodor et al., "Light-Directed, Spatially Addressable Parallel Chemical Synthesis," *Science*, 251:767-773, Feb. 1991.
Gao et al., "Screening Derivatized Peptide Libraries for Tight Binding Inhibitors to Carbonic Anhydrase II by Electrospray Ionization-Mass Spectrometry," *J. Med. Chem.*, 39:1949-1955, 1996.
Gubler et al., "A simple and very efficient method for generating cDNA libraries," *Gene*, 25:263-269, 1983.
Hajduk et al., "High-Throughput Nuclear Magnetic Resonance-Based Screening," *J. Med. Chem.* vol. 42, pp. 2315-2317, 1999.
Harlow et al., *Using Antibodies, A Laboratory Manual*, (1999) Cold Spring Harbor Press.
Huls et al., "A recombinant, fully human monoclonal antibody with antitumor activity constructed from phage-displayed antibody fragments," *Nature Biotechnology*, 17:276-281, Mar. 1999.
Innis et al., *PCR Protocols—A guide to Methods and Applications* (1990) Academic Press, Inc.
Kay et al., *Phage Display of Peptides and Proteins* (1996) Academic Press, Inc.

(Continued)

Primary Examiner — Maury Audet
Assistant Examiner — Roy Teller
(74) *Attorney, Agent, or Firm* — Danisco US Inc.

(57) ABSTRACT

The invention is directed to peptides. Specifically, the invention is directed to peptides which bind skin and do not bind hair. Alternatively, the invention is drawn to peptides which bind hair and do not bind skin.

4 Claims, 2 Drawing Sheets

(56) References Cited

OTHER PUBLICATIONS

Kenny and Fowell, Eds., *Practical Protein Chromatography Methods in Molecular Biology*, vol. 11, (1992) Humana Press, Totowa, N.J.

Lam et al., "The Chemical Synthesis of Large Random Peptide Libraries and Their Use for the Discovery of Ligands for Macromolecular Acceptors," *Bioorganic & Medicinal Chemistry Letters*, 3(3):419-424, 1993.

Marshall et al., "Fourier Transform Ion Cyclotron Resonance Mass Spectrometry: A Primer," *Mass Spectrometry Reviews*, 17:1-35, 1998.

Morton et al., "Kinetic Analysis of Macromolecular Interactions Using Surface Plasmon Resonance Biosensors," *Methods in Enzymology*, 295:268-294, 1998.

Nelson et al., Advances in surface plasmon resonance biomoleculr interaction analysis mass spectrometry (BIA/MS), *J. Molecular Recognition*, 12:77-93, 1999.

Pinilla et al., "Investigation of antigen-antibody interactions using a soluable, non-support-bound synthetic decapeptide library composed of four trillion ($4 \times 10^{12}$) sequences," *Biochem. J.*, 301:847-853, 1994.

Sagarin, E., *Cosmetics, Science & Technology*. $2^{nd}$ ed., vol. 1, pp. 189 et seq., 1972.

Sambrook et al., *Molecular Cloning—A Laboratory Manual*, $2^{nd}$ ed., vol. 1-3, Cold Springs Harbor Publishing, 1989.

Scott et al., "Searching for Peptide Ligands with an Epitope Library," *Science*, vol. 249, pp. 386-390, Jul. 1990.

Singleton et al., *Dictionary of Microbiology and Molecular Biology*, $2^{nd}$ ed., p. 35.

Smith, G.P., "Filamentous Fusion Phage: Novel Expression Vectors That Display Cloned Antigens on the Virion Surface," *Science*, vol. 228, pp. 1315-1317, Jun. 1985.

Stemmer, Willem P. C., "DNA shuffling by random fragmentation and reassembly: In vitro recombination for molecular evolution," *Proc. Natl. Acad. Sci.*, USA, 91:10747-10751, 1994.

Szabo et al., "Surface plasmon resonance and its use in biomolecular interaction analysis (BIA)," *Current Opinion in Structural Biology*, vol. 5, pp. 699-705, 1995.

Tjoeng et al., "Multiple peptide synthesis using a single support (MPS3)," *Int. J. Peptide Protein Res.*, vol. 35, pp. 141-146, 1990.

Walk et al., "ESI Fourier Transform Ion Cyclotron Resonance Mass Spectrometry, (ESI-FT-ICR-MS): A Rapid High-Resolution Analytical Method for Combinatorial Compound Libraries," *Angew. Chem. Int. Ed.*, vol. 38, No. 12, pp. 1763-1765, 1999.

Wu et al., "Quantitative electrospray mass spectrometry for the rapid assay of enzyme inhibitors," *Chemistry & Biology*, 4(9):653-657, 1997.

Youngquist et al., "Generation and Screening of Combinatorial Peptide Libraries Designed for Rapid Sequencing by Mass Spectrometry," *J. Am. Chem. Soc.*, 117:3900-3906, 1995.

SEQUENCE LISTING

```
<160> NUMBER OF SEQ ID NOS: 111

<210> SEQ ID NO 1
<211> LENGTH: 12
<212> TYPE: PRT
<213> ORGANISM: Artificial Sequence
<220> FEATURE:
<223> OTHER INFORMATION: synthetic skin binding peptide

<400> SEQUENCE: 1

Lys Gln Ala Thr Phe Pro Pro Asn Pro Thr Ala Tyr
1               5                   10

<210> SEQ ID NO 2
<211> LENGTH: 7
<212> TYPE: PRT
<213> ORGANISM: Artificial Sequence
<220> FEATURE:
<223> OTHER INFORMATION: synthetic skin binding peptide

<400> SEQUENCE: 2

Gln Ala Thr Phe Met Tyr Asn
1               5

<210> SEQ ID NO 3
<211> LENGTH: 12
<212> TYPE: PRT
<213> ORGANISM: Artificial Sequence
<220> FEATURE:
<223> OTHER INFORMATION: synthetic skin binding peptide

<400> SEQUENCE: 3

His Gly His Met Val Ser Thr Ser Gln Leu Ser Ile
1               5                   10

<210> SEQ ID NO 4
<211> LENGTH: 11
<212> TYPE: PRT
<213> ORGANISM: Artificial Sequence
<220> FEATURE:
<223> OTHER INFORMATION: synthetic skin binding peptide

<400> SEQUENCE: 4

Val Leu Thr Ser Gln Leu Pro Asn His Ser Met
1               5                   10

<210> SEQ ID NO 5
```

-continued

```
<211> LENGTH: 7
<212> TYPE: PRT
<213> ORGANISM: Artificial Sequence
<220> FEATURE:
<223> OTHER INFORMATION: synthetic skin binding peptide

<400> SEQUENCE: 5

Leu Ser Pro Ser Arg Met Lys
1               5

<210> SEQ ID NO 6
<211> LENGTH: 7
<212> TYPE: PRT
<213> ORGANISM: Artificial Sequence
<220> FEATURE:
<223> OTHER INFORMATION: synthetic skin binding peptide

<400> SEQUENCE: 6

Leu Pro Ile Pro Arg Met Lys
1               5

<210> SEQ ID NO 7
<211> LENGTH: 7
<212> TYPE: PRT
<213> ORGANISM: Artificial Sequence
<220> FEATURE:
<223> OTHER INFORMATION: synthetic skin binding peptide

<400> SEQUENCE: 7

His Ser Thr Ala Tyr Leu Thr
1               5

<210> SEQ ID NO 8
<211> LENGTH: 7
<212> TYPE: PRT
<213> ORGANISM: Artificial Sequence
<220> FEATURE:
<223> OTHER INFORMATION: synthetic skin binding peptide

<400> SEQUENCE: 8

His Gln Arg Pro Tyr Leu Thr
1               5

<210> SEQ ID NO 9
<211> LENGTH: 12
<212> TYPE: PRT
<213> ORGANISM: Artificial Sequence
<220> FEATURE:
<223> OTHER INFORMATION: synthetic skin binding peptide

<400> SEQUENCE: 9

Ala Pro Gln Gln Arg Pro Met Lys Thr Phe Asn Thr
1               5                   10

<210> SEQ ID NO 10
<211> LENGTH: 12
<212> TYPE: PRT
<213> ORGANISM: Artificial Sequence
<220> FEATURE:
<223> OTHER INFORMATION: synthetic skin binding peptide

<400> SEQUENCE: 10

Ala Pro Gln Gln Arg Pro Met Lys Thr Val Gln Tyr
1               5                   10

<210> SEQ ID NO 11
<211> LENGTH: 7
<212> TYPE: PRT
```

```
<213> ORGANISM: Artificial Sequence
<220> FEATURE:
<223> OTHER INFORMATION: synthetic skin binding peptide

<400> SEQUENCE: 11

Pro Pro Trp Leu Asp Leu Leu
  1               5

<210> SEQ ID NO 12
<211> LENGTH: 7
<212> TYPE: PRT
<213> ORGANISM: Artificial Sequence
<220> FEATURE:
<223> OTHER INFORMATION: synthetic skin binding peptide

<400> SEQUENCE: 12

Pro Pro Trp Thr Phe Pro Leu
  1               5

<210> SEQ ID NO 13
<211> LENGTH: 7
<212> TYPE: PRT
<213> ORGANISM: Artificial Sequence
<220> FEATURE:
<223> OTHER INFORMATION: synthetic skin binding peptide

<400> SEQUENCE: 13

Ser Val Thr His Leu Thr Ser
  1               5

<210> SEQ ID NO 14
<211> LENGTH: 7
<212> TYPE: PRT
<213> ORGANISM: Artificial Sequence
<220> FEATURE:
<223> OTHER INFORMATION: synthetic skin binding peptide

<400> SEQUENCE: 14

Val Ile Thr Arg Leu Thr Ser
  1               5

<210> SEQ ID NO 15
<211> LENGTH: 7
<212> TYPE: PRT
<213> ORGANISM: Artificial Sequence
<220> FEATURE:
<223> OTHER INFORMATION: synthetic skin binding peptide

<400> SEQUENCE: 15

Phe Pro Pro Leu Leu Arg Leu
  1               5

<210> SEQ ID NO 16
<211> LENGTH: 12
<212> TYPE: PRT
<213> ORGANISM: Artificial Sequence
<220> FEATURE:
<223> OTHER INFORMATION: synthetic skin binding peptide

<400> SEQUENCE: 16

Asp Leu Lys Pro Pro Leu Leu Ala Leu Ser Lys Val
  1               5                  10

<210> SEQ ID NO 17
<211> LENGTH: 12
<212> TYPE: PRT
<213> ORGANISM: Artificial Sequence
<220> FEATURE:
```

-continued

<223> OTHER INFORMATION: synthetic skin binding peptide

<400> SEQUENCE: 17

Ser His Pro Ser Gly Ala Leu Gln Glu Gly Thr Phe
1               5                   10

<210> SEQ ID NO 18
<211> LENGTH: 12
<212> TYPE: PRT
<213> ORGANISM: Artificial Sequence
<220> FEATURE:
<223> OTHER INFORMATION: synthetic skin binding peptide

<400> SEQUENCE: 18

Phe Pro Leu Thr Ser Lys Pro Ser Gly Ala Cys Thr
1               5                   10

<210> SEQ ID NO 19
<211> LENGTH: 12
<212> TYPE: PRT
<213> ORGANISM: Artificial Sequence
<220> FEATURE:
<223> OTHER INFORMATION: synthetic skin binding peptide

<400> SEQUENCE: 19

Asp Leu Lys Pro Pro Leu Leu Ala Leu Ser Lys Val
1               5                   10

<210> SEQ ID NO 20
<211> LENGTH: 7
<212> TYPE: PRT
<213> ORGANISM: Artificial Sequence
<220> FEATURE:
<223> OTHER INFORMATION: synthetic skin binding peptide

<400> SEQUENCE: 20

Pro Leu Leu Ala Leu His Ser
1               5

<210> SEQ ID NO 21
<211> LENGTH: 7
<212> TYPE: PRT
<213> ORGANISM: Artificial Sequence
<220> FEATURE:
<223> OTHER INFORMATION: synthetic skin binding peptide

<400> SEQUENCE: 21

Tyr Pro Ile Ser Thr Gln Ile
1               5

<210> SEQ ID NO 22
<211> LENGTH: 12
<212> TYPE: PRT
<213> ORGANISM: Artificial Sequence
<220> FEATURE:
<223> OTHER INFORMATION: synthetic skin binding peptide

<400> SEQUENCE: 22

Tyr Ala Lys Gln His Tyr Pro Ile Ser Thr Phe Lys
1               5                   10

<210> SEQ ID NO 23
<211> LENGTH: 7
<212> TYPE: PRT
<213> ORGANISM: Artificial Sequence
<220> FEATURE:
<223> OTHER INFORMATION: synthetic skin binding peptide

```
<400> SEQUENCE: 23

His Ser Thr Ala Tyr Leu Thr
1               5

<210> SEQ ID NO 24
<211> LENGTH: 12
<212> TYPE: PRT
<213> ORGANISM: Artificial Sequence
<220> FEATURE:
<223> OTHER INFORMATION: synthetic skin binding peptide

<400> SEQUENCE: 24

Ser Thr Ala Tyr Leu Val Ala Met Ser Ala Ala Pro
1               5                   10

<210> SEQ ID NO 25
<211> LENGTH: 12
<212> TYPE: PRT
<213> ORGANISM: Artificial Sequence
<220> FEATURE:
<223> OTHER INFORMATION: synthetic skin binding cluster sequence
<221> NAME/KEY: VARIANT
<222> LOCATION: 8, 10, 11, 12
<223> OTHER INFORMATION: Xaa = Any L-Amino Acid

<400> SEQUENCE: 25

Ala Pro Gln Gln Arg Pro Met Xaa Thr Xaa Xaa Xaa
1               5                   10

<210> SEQ ID NO 26
<211> LENGTH: 7
<212> TYPE: PRT
<213> ORGANISM: Artificial Sequence
<220> FEATURE:
<223> OTHER INFORMATION: synthetic skin binding cluster sequence
<221> NAME/KEY: VARIANT
<222> LOCATION: (4)...(6)
<223> OTHER INFORMATION: Xaa = Any L-Amino Acid

<400> SEQUENCE: 26

Pro Pro Trp Xaa Xaa Xaa Leu
1               5

<210> SEQ ID NO 27
<211> LENGTH: 7
<212> TYPE: PRT
<213> ORGANISM: Artificial Sequence
<220> FEATURE:
<223> OTHER INFORMATION: synthetic skin binding cluster sequence
<221> NAME/KEY: VARIANT
<222> LOCATION: 1, 2, 4
<223> OTHER INFORMATION: Xaa = Any L-Amino Acid

<400> SEQUENCE: 27

Xaa Xaa Thr Xaa Leu Thr Ser
1               5

<210> SEQ ID NO 28
<211> LENGTH: 7
<212> TYPE: PRT
<213> ORGANISM: Artificial Sequence
<220> FEATURE:
<223> OTHER INFORMATION: synthetic skin binding cluster sequence
<221> NAME/KEY: VARIANT
<222> LOCATION: 1, 6
<223> OTHER INFORMATION: Xaa = Any L-Amino Acid

<400> SEQUENCE: 28

Xaa Pro Pro Leu Leu Xa

```
<210> SEQ ID NO 29
<211> LENGTH: 7
<212> TYPE: PRT
<213> ORGANISM: Artificial Sequence
<220> FEATURE:
<223> OTHER INFORMATION: synthetic skin binding cluster sequence
<221> NAME/KEY: VARIANT
<222> LOCATION: 2, 7
<223> OTHER INFORMATION: Xaa = Any L-Amino Acid

<400> SEQUENCE: 29

Ser Xaa Pro Ser Gly Ala Xaa
 1               5

<210> SEQ ID NO 30
<211> LENGTH: 12
<212> TYPE: PRT
<213> ORGANISM: Artificial Sequence
<220> FEATURE:
<223> OTHER INFORMATION: synthetic skin binding cluster sequence
<221> NAME/KEY: VARIANT
<222> LOCATION: 1, 6, 7, 9, 10, 11, 12
<223> OTHER INFORMATION: Xaa = Any L-Amino Acid

<400> SEQUENCE: 30

Xaa Gln Ala Thr Phe Xaa Xaa Asn Xaa Xaa Xaa Xaa
 1               5                  10

<210> SEQ ID NO 31
<211> LENGTH: 12
<212> TYPE: PRT
<213> ORGANISM: Artificial Sequence
<220> FEATURE:
<223> OTHER INFORMATION: synthetic skin binding cluster sequence
<221> NAME/KEY: VARIANT
<222> LOCATION: 2, 7, 8, 9, 10, 11, 12
<223> OTHER INFORMATION: Xaa = Any L-Amino Acid

<400> SEQUENCE: 31

Val Xaa Thr Ser Gln Leu Xaa Xaa Xaa Xaa Xaa Xaa
 1               5                  10

<210> SEQ ID NO 32
<211> LENGTH: 7
<212> TYPE: PRT
<213> ORGANISM: Artificial Sequence
<220> FEATURE:
<223> OTHER INFORMATION: synthetic skin binding cluster sequence
<221> NAME/KEY: VARIANT
<222> LOCATION: (2)...(4)
<223> OTHER INFORMATION: Xaa = Any L-Amino Acid

<400> SEQUENCE: 32

Leu Xaa Xaa Xaa Arg Met Lys
 1               5

<210> SEQ ID NO 33
<211> LENGTH: 7
<212> TYPE: PRT
<213> ORGANISM: Artificial Sequence
<220> FEATURE:
<223> OTHER INFORMATION: synthetic skin binding cluster sequence
<221> NAME/KEY: VARIANT
<222> LOCATION: (2)...(4)
<223> OTHER INFORMATION: Xaa = Any L-Amino Acid

<400> SEQUENCE: 33

His Xaa Xaa Xaa Tyr Leu Thr
```

<210> SEQ ID NO 34
<211> LENGTH: 7
<212> TYPE: PRT
<213> ORGANISM: Artificial Sequence
<220> FEATURE:
<223> OTHER INFORMATION: synthetic hair binding peptide

<400> SEQUENCE: 34

Asn Thr Pro Lys Glu Asn Trp
1               5

<210> SEQ ID NO 35
<211> LENGTH: 7
<212> TYPE: PRT
<213> ORGANISM: Artificial Sequence
<220> FEATURE:
<223> OTHER INFORMATION: synthetic hair binding peptide

<400> SEQUENCE: 35

Asn Thr Pro Ala Ser Asn Arg
1               5

<210> SEQ ID NO 36
<211> LENGTH: 7
<212> TYPE: PRT
<213> ORGANISM: Artificial Sequence
<220> FEATURE:
<223> OTHER INFORMATION: synthetic hair binding peptide

<400> SEQUENCE: 36

Pro Arg Gly Met Leu Ser Thr
1               5

<210> SEQ ID NO 37
<211> LENGTH: 7
<212> TYPE: PRT
<213> ORGANISM: Artificial Sequence
<220> FEATURE:
<223> OTHER INFORMATION: synthetic hair binding peptide

<400> SEQUENCE: 37

Pro Pro Thr Tyr Leu Ser Thr
1               5

<210> SEQ ID NO 38
<211> LENGTH: 12
<212> TYPE: PRT
<213> ORGANISM: Artificial Sequence
<220> FEATURE:
<223> OTHER INFORMATION: synthetic hair binding peptide

<400> SEQUENCE: 38

Thr Ile Pro Thr His Arg Gln His Asp Tyr Arg Ser
1               5                   10

<210> SEQ ID NO 39
<211> LENGTH: 7
<212> TYPE: PRT
<213> ORGANISM: Artificial Sequence
<220> FEATURE:
<223> OTHER INFORMATION: synthetic hair binding peptide

<400> SEQUENCE: 39

Thr Pro Pro Thr His Arg Leu
1               5

```
<210> SEQ ID NO 40
<211> LENGTH: 7
<212> TYPE: PRT
<213> ORGANISM: Artificial Sequence
<220> FEATURE:
<223> OTHER INFORMATION: synthetic hair binding peptide

<400> SEQUENCE: 40

Leu Pro Thr Met Ser Thr Pro
 1               5

<210> SEQ ID NO 41
<211> LENGTH: 7
<212> TYPE: PRT
<213> ORGANISM: Artificial Sequence
<220> FEATURE:
<223> OTHER INFORMATION: synthetic hair binding peptide

<400> SEQUENCE: 41

Leu Gly Thr Asn Ser Thr Pro
 1               5

<210> SEQ ID NO 42
<211> LENGTH: 12
<212> TYPE: PRT
<213> ORGANISM: Artificial Sequence
<220> FEATURE:
<223> OTHER INFORMATION: synthetic hair binding peptide

<400> SEQUENCE: 42

Thr Pro Leu Thr Gly Ser Thr Asn Leu Leu Ser Ser
 1               5                  10

<210> SEQ ID NO 43
<211> LENGTH: 7
<212> TYPE: PRT
<213> ORGANISM: Artificial Sequence
<220> FEATURE:
<223> OTHER INFORMATION: synthetic hair binding peptide

<400> SEQUENCE: 43

Thr Pro Leu Thr Lys Glu Thr
 1               5

<210> SEQ ID NO 44
<211> LENGTH: 7
<212> TYPE: PRT
<213> ORGANISM: Artificial Sequence
<220> FEATURE:
<223> OTHER INFORMATION: synthetic hair binding peptide

<400> SEQUENCE: 44

Lys Gln Ser His Asn Pro Pro
 1               5

<210> SEQ ID NO 45
<211> LENGTH: 7
<212> TYPE: PRT
<213> ORGANISM: Artificial Sequence
<220> FEATURE:
<223> OTHER INFORMATION: synthetic hair binding peptide

<400> SEQUENCE: 45

Gln Gln Ser His Asn Pro Pro
 1               5

<210> SEQ ID NO 46
```

```
<211> LENGTH: 7
<212> TYPE: PRT
<213> ORGANISM: Artificial Sequence
<220> FEATURE:
<223> OTHER INFORMATION: synthetic hair binding peptide

<400> SEQUENCE: 46

Thr Gln Pro His Asn Pro Pro
 1               5

<210> SEQ ID NO 47
<211> LENGTH: 12
<212> TYPE: PRT
<213> ORGANISM: Artificial Sequence
<220> FEATURE:
<223> OTHER INFORMATION: synthetic hair binding peptide

<400> SEQUENCE: 47

Ser Thr Asn Leu Leu Arg Thr Ser Thr Val His Pro
 1               5                  10

<210> SEQ ID NO 48
<211> LENGTH: 12
<212> TYPE: PRT
<213> ORGANISM: Artificial Sequence
<220> FEATURE:
<223> OTHER INFORMATION: synthetic hair binding peptide

<400> SEQUENCE: 48

His Thr Gln Pro Ser Tyr Ser Ser Thr Asn Leu Phe
 1               5                  10

<210> SEQ ID NO 49
<211> LENGTH: 7
<212> TYPE: PRT
<213> ORGANISM: Artificial Sequence
<220> FEATURE:
<223> OTHER INFORMATION: synthetic hair binding peptide

<400> SEQUENCE: 49

Ser Leu Leu Ser Ser His Ala
 1               5

<210> SEQ ID NO 50
<211> LENGTH: 12
<212> TYPE: PRT
<213> ORGANISM: Artificial Sequence
<220> FEATURE:
<223> OTHER INFORMATION: synthetic hair binding peptide

<400> SEQUENCE: 50

Gln Gln Ser Ser Ile Ser Leu Ser Ser His Ala Val
 1               5                  10

<210> SEQ ID NO 51
<211> LENGTH: 7
<212> TYPE: PRT
<213> ORGANISM: Artificial Sequence
<220> FEATURE:
<223> OTHER INFORMATION: synthetic hair binding peptide

<400> SEQUENCE: 51

Asn Ala Ser Pro Ser Ser Leu
 1               5

<210> SEQ ID NO 52
<211> LENGTH: 7
<212> TYPE: PRT
```

```
<213> ORGANISM: Artificial Sequence
<220> FEATURE:
<223> OTHER INFORMATION: synthetic hair binding peptide

<400> SEQUENCE: 52

His Ser Pro Ser Ser Leu Arg
 1               5

<210> SEQ ID NO 53
<211> LENGTH: 7
<212> TYPE: PRT
<213> ORGANISM: Artificial Sequence
<220> FEATURE:
<223> OTHER INFORMATION: synthetic hair binding peptide
<221> NAME/KEY: VARIANT
<222> LOCATION: 2
<223> OTHER INFORMATION: Xaa = His, Arg, or Asn

<400> SEQUENCE: 53

Lys Xaa Ser His His Thr His
 1               5

<210> SEQ ID NO 54
<211> LENGTH: 7
<212> TYPE: PRT
<213> ORGANISM: Artificial Sequence
<220> FEATURE:
<223> OTHER INFORMATION: synthetic hair binding peptide
<221> NAME/KEY: VARIANT
<222> LOCATION: 2
<223> OTHER INFORMATION: Xaa = His, Arg, or Asn

<400> SEQUENCE: 54

Glu Xaa Ser His His Thr His
 1               5

<210> SEQ ID NO 55
<211> LENGTH: 12
<212> TYPE: PRT
<213> ORGANISM: Artificial Sequence
<220> FEATURE:
<223> OTHER INFORMATION: synthetic hair binding peptide

<400> SEQUENCE: 55

Ser His His Thr His Tyr Gly Gln Pro Gly Pro Val
 1               5                   10

<210> SEQ ID NO 56
<211> LENGTH: 7
<212> TYPE: PRT
<213> ORGANISM: Artificial Sequence
<220> FEATURE:
<223> OTHER INFORMATION: synthetic hair binding peptide

<400> SEQUENCE: 56

Leu Glu Ser Thr Ser Leu Leu
 1               5

<210> SEQ ID NO 57
<211> LENGTH: 7
<212> TYPE: PRT
<213> ORGANISM: Artificial Sequence
<220> FEATURE:
<223> OTHER INFORMATION: synthetic hair binding cluster sequence
<221> NAME/KEY: VARIANT
<222> LOCATION: 4, 5, 7
<223> OTHER INFORMATION: Xaa = Any L-Amino Acid

<400> SEQUENCE: 57
```

Asn Thr Pro Xaa Xaa Asn Xaa
1               5

<210> SEQ ID NO 58
<211> LENGTH: 7
<212> TYPE: PRT
<213> ORGANISM: Artificial Sequence
<220> FEATURE:
<223> OTHER INFORMATION: synthetic hair binding cluster sequence
<221> NAME/KEY: VARIANT
<222> LOCATION: (2)...(4)
<223> OTHER INFORMATION: Xaa = Any L-Amino Acid

<400> SEQUENCE: 58

Pro Xaa Xaa Xaa Leu Ser Thr
1               5

<210> SEQ ID NO 59
<211> LENGTH: 7
<212> TYPE: PRT
<213> ORGANISM: Artificial Sequence
<220> FEATURE:
<223> OTHER INFORMATION: synthetic hair binding cluster sequence
<221> NAME/KEY: VARIANT
<222> LOCATION: 2, 7
<223> OTHER INFORMATION: Xaa = Any L-Amino Acid

<400> SEQUENCE: 59

Thr Xaa Pro Thr His Arg Xaa
1               5

<210> SEQ ID NO 60
<211> LENGTH: 7
<212> TYPE: PRT
<213> ORGANISM: Artificial Sequence
<220> FEATURE:
<223> OTHER INFORMATION: synthetic hair binding cluster sequence
<221> NAME/KEY: VARIANT
<222> LOCATION: 2, 4
<223> OTHER INFORMATION: Xaa = Any L-Amino Acid

<400> SEQUENCE: 60

Leu Xaa Thr Xaa Ser Thr Pro
1               5

<210> SEQ ID NO 61
<211> LENGTH: 7
<212> TYPE: PRT
<213> ORGANISM: Artificial Sequence
<220> FEATURE:
<223> OTHER INFORMATION: synthetic hair binding cluster sequence
<221> NAME/KEY: VARIANT
<222> LOCATION: 5, 6
<223> OTHER INFORMATION: Xaa = Any L-Amino Acid

<400> SEQUENCE: 61

Thr Pro Leu Thr Xaa Xaa Thr
1               5

<210> SEQ ID NO 62
<211> LENGTH: 7
<212> TYPE: PRT
<213> ORGANISM: Artificial Sequence
<220> FEATURE:
<223> OTHER INFORMATION: synthetic hair binding cluster sequence
<221> NAME/KEY: VARIANT
<222> LOCATION: 1, 3
<223> OTHER INFORMATION: Xaa = Any L-Amino Acid

<400> SEQUENCE: 62

Xaa Gln Xaa His Asn Pro Pro
1               5

<210> SEQ ID NO 63
<211> LENGTH: 34
<212> TYPE: DNA
<213> ORGANISM: Artificial Sequence
<220> FEATURE:
<223> OTHER INFORMATION: primer

<400> SEQUENCE: 63
cgtagtggca ttacgtattt tacccgttta atgg           34

<210> SEQ ID NO 64
<211> LENGTH: 34
<212> TYPE: DNA
<213> ORGANISM: Artificial Sequence
<220> FEATURE:
<223> OTHER INFORMATION: primer

<400> SEQUENCE: 64
cgagagggtt gatataagta tagcccggaa tagg           34

<210> SEQ ID NO 65
<211> LENGTH: 24
<212> TYPE: DNA
<213> ORGANISM: Artificial Sequence
<220> FEATURE:
<223> OTHER INFORMATION: primer

<400> SEQUENCE: 65
cctcgaaagc aagctgataa accg                      24

<210> SEQ ID NO 66
<211> LENGTH: 23
<212> TYPE: DNA
<213> ORGANISM: Artificial Sequence
<220> FEATURE:
<223> OTHER INFORMATION: primer

<400> SEQUENCE: 66
cattccacag acaaccctca tag                       23

<210> SEQ ID NO 67
<211> LENGTH: 4
<212> TYPE: PRT
<213> ORGANISM: Artificial Sequence
<220> FEATURE:
<223> OTHER INFORMATION: synthetic skin binding peptide repeatable motif

<400> SEQUENCE: 67

Gln Ala Thr Phe
1

<210> SEQ ID NO 68
<211> LENGTH: 4
<212> TYPE: PRT
<213> ORGANISM: Artificial Sequence
<220> FEATURE:
<223> OTHER INFORMATION: synthetic skin binding peptide repeatable motif

<400> SEQUENCE: 68

Thr Ser Gln Leu
1

<210> SEQ ID NO 69
<211> LENGTH: 7

```
<212> TYPE: PRT
<213> ORGANISM: Artificial Sequence
<220> FEATURE:
<223> OTHER INFORMATION: synthetic skin binding peptide repeatable motif

<400> SEQUENCE: 69

Ala Pro Gln Gln Arg Pro Met
 1               5

<210> SEQ ID NO 70
<211> LENGTH: 4
<212> TYPE: PRT
<213> ORGANISM: Artificial Sequence
<220> FEATURE:
<223> OTHER INFORMATION: synthetic skin binding peptide repeatable motif

<400> SEQUENCE: 70

Pro Met Lys Thr
 1

<210> SEQ ID NO 71
<211> LENGTH: 4
<212> TYPE: PRT
<213> ORGANISM: Artificial Sequence
<220> FEATURE:
<223> OTHER INFORMATION: synthetic skin binding peptide repeatable motif

<400> SEQUENCE: 71

Pro Pro Leu Leu
 1

<210> SEQ ID NO 72
<211> LENGTH: 8
<212> TYPE: PRT
<213> ORGANISM: Artificial Sequence
<220> FEATURE:
<223> OTHER INFORMATION: synthetic skin binding peptide repeatable motif

<400> SEQUENCE: 72

Ala Pro Gln Gln Arg Met Lys Thr
 1               5

<210> SEQ ID NO 73
<211> LENGTH: 4
<212> TYPE: PRT
<213> ORGANISM: Artificial Sequence
<220> FEATURE:
<223> OTHER INFORMATION: synthetic skin binding peptide repeatable motif

<400> SEQUENCE: 73

Pro Ser Gly Ala
 1

<210> SEQ ID NO 74
<211> LENGTH: 5
<212> TYPE: PRT
<213> ORGANISM: Artificial Sequence
<220> FEATURE:
<223> OTHER INFORMATION: synthetic skin binding peptide repeatable motif

<400> SEQUENCE: 74

Pro Leu Leu Ala Leu
 1               5

<210> SEQ ID NO 75
<211> LENGTH: 5
<212> TYPE: PRT
<213> ORGANISM: Artificial Sequence
```

```
<220> FEATURE:
<223> OTHER INFORMATION: synthetic skin binding peptide repeatable motif

<400> SEQUENCE: 75

Ser Thr Ala Tyr Leu
1               5

<210> SEQ ID NO 76
<211> LENGTH: 5
<212> TYPE: PRT
<213> ORGANISM: Artificial Sequence
<220> FEATURE:
<223> OTHER INFORMATION: synthetic skin binding peptide repeatable motif

<400> SEQUENCE: 76

Tyr Pro Ile Ser Thr
1               5

<210> SEQ ID NO 77
<211> LENGTH: 4
<212> TYPE: PRT
<213> ORGANISM: Artificial Sequence
<220> FEATURE:
<223> OTHER INFORMATION: synthetic hair binding peptide repeatable motif

<400> SEQUENCE: 77

Ser Thr Asn Leu
1

<210> SEQ ID NO 78
<211> LENGTH: 5
<212> TYPE: PRT
<213> ORGANISM: Artificial Sequence
<220> FEATURE:
<223> OTHER INFORMATION: synthetic hair binding peptide repeatable motif

<400> SEQUENCE: 78

Leu Ser Ser His Ala
1               5

<210> SEQ ID NO 79
<211> LENGTH: 5
<212> TYPE: PRT
<213> ORGANISM: Artificial Sequence
<220> FEATURE:
<223> OTHER INFORMATION: synthetic hair binding peptide repeatable motif

<400> SEQUENCE: 79

Ser Pro Ser Ser Leu
1               5

<210> SEQ ID NO 80
<211> LENGTH: 5
<212> TYPE: PRT
<213> ORGANISM: Artificial Sequence
<220> FEATURE:
<223> OTHER INFORMATION: synthetic hair binding peptide repeatable motif

<400> SEQUENCE: 80

Ser His His Thr His
1               5

<210> SEQ ID NO 81
<211> LENGTH: 4
<212> TYPE: PRT
<213> ORGANISM: Artificial Sequence
<220> FEATURE:
<223> OTHER INFORMATION: synthetic hair binding peptide repeatable motif
```

```
<400> SEQUENCE: 81

Pro Thr His Arg
 1

<210> SEQ ID NO 82
<211> LENGTH: 4
<212> TYPE: PRT
<213> ORGANISM: Artificial Sequence
<220> FEATURE:
<223> OTHER INFORMATION: synthetic hair binding peptide repeatable motif

<400> SEQUENCE: 82

Thr Pro Leu Thr
 1

<210> SEQ ID NO 83
<211> LENGTH: 4
<212> TYPE: PRT
<213> ORGANISM: Artificial Sequence
<220> FEATURE:
<223> OTHER INFORMATION: synthetic hair binding peptide repeatable motif

<400> SEQUENCE: 83

His Asn Pro Pro
 1

<210> SEQ ID NO 84
<211> LENGTH: 9
<212> TYPE: PRT
<213> ORGANISM: Artificial Sequence
<220> FEATURE:
<223> OTHER INFORMATION: synthetic skin binding peptide derivative

<400> SEQUENCE: 84

Cys Gln Ala Thr Phe Met Tyr Asn Cys
 1               5

<210> SEQ ID NO 85
<211> LENGTH: 8
<212> TYPE: PRT
<213> ORGANISM: Artificial Sequence
<220> FEATURE:
<223> OTHER INFORMATION: synthetic skin binding peptide derivative

<400> SEQUENCE: 85

Leu Ser Pro Ser Arg Met Lys Cys
 1               5

<210> SEQ ID NO 86
<211> LENGTH: 9
<212> TYPE: PRT
<213> ORGANISM: Artificial Sequence
<220> FEATURE:
<223> OTHER INFORMATION: synthetic skin binding peptide derivative

<400> SEQUENCE: 86

Cys Leu Pro Ile Pro Arg Met Lys Cys
 1               5

<210> SEQ ID NO 87
<211> LENGTH: 9
<212> TYPE: PRT
<213> ORGANISM: Artificial Sequence
<220> FEATURE:
<223> OTHER INFORMATION: synthetic skin binding peptide derivative

<400> SEQUENCE: 87
```

Cys His Ser Thr Ala Tyr Leu Thr Cys
1               5

<210> SEQ ID NO 88
<211> LENGTH: 9
<212> TYPE: PRT
<213> ORGANISM: Artificial Sequence
<220> FEATURE:
<223> OTHER INFORMATION: synthetic skin binding peptide derivative

<400> SEQUENCE: 88

Cys His Gln Arg Pro Tyr Leu Thr Cys
1               5

<210> SEQ ID NO 89
<211> LENGTH: 9
<212> TYPE: PRT
<213> ORGANISM: Artificial Sequence
<220> FEATURE:
<223> OTHER INFORMATION: synthetic skin binding peptide derivative

<400> SEQUENCE: 89

Cys Pro Pro Trp Leu Asp Leu Leu Cys
1               5

<210> SEQ ID NO 90
<211> LENGTH: 9
<212> TYPE: PRT
<213> ORGANISM: Artificial Sequence
<220> FEATURE:
<223> OTHER INFORMATION: synthetic skin binding peptide derivative

<400> SEQUENCE: 90

Cys Pro Pro Trp Thr Phe Pro Leu Cys
1               5

<210> SEQ ID NO 91
<211> LENGTH: 9
<212> TYPE: PRT
<213> ORGANISM: Artificial Sequence
<220> FEATURE:
<223> OTHER INFORMATION: synthetic skin binding peptide derivative

<400> SEQUENCE: 91

Cys Ser Val Thr His Leu Thr Ser Cys
1               5

<210> SEQ ID NO 92
<211> LENGTH: 9
<212> TYPE: PRT
<213> ORGANISM: Artificial Sequence
<220> FEATURE:
<223> OTHER INFORMATION: synthetic skin binding peptide derivative

<400> SEQUENCE: 92

Cys Val Ile Thr Arg Leu Thr Ser Cys
1               5

<210> SEQ ID NO 93
<211> LENGTH: 9
<212> TYPE: PRT
<213> ORGANISM: Artificial Sequence
<220> FEATURE:
<223> OTHER INFORMATION: synthetic skin binding peptide derivative

<400> SEQUENCE: 93

Cys Phe Pro Pro Leu Leu Arg Leu Cys

<210> SEQ ID NO 94
<211> LENGTH: 9
<212> TYPE: PRT
<213> ORGANISM: Artificial Sequence
<220> FEATURE:
<223> OTHER INFORMATION: synthetic skin binding peptide derivative

<400> SEQUENCE: 94

Cys Pro Leu Leu Ala Leu His Ser Cys
1               5

<210> SEQ ID NO 95
<211> LENGTH: 9
<212> TYPE: PRT
<213> ORGANISM: Artificial Sequence
<220> FEATURE:
<223> OTHER INFORMATION: synthetic skin binding peptide derivative

<400> SEQUENCE: 95

Cys Tyr Pro Ile Ser Thr Gln Ile Cys
1               5

<210> SEQ ID NO 96
<211> LENGTH: 9
<212> TYPE: PRT
<213> ORGANISM: Artificial Sequence
<220> FEATURE:
<223> OTHER INFORMATION: synthetic skin binding peptide derivative

<400> SEQUENCE: 96

Cys His Ser Thr Ala Tyr Leu Thr Cys
1               5

<210> SEQ ID NO 97
<211> LENGTH: 9
<212> TYPE: PRT
<213> ORGANISM: Artificial Sequence
<220> FEATURE:
<223> OTHER INFORMATION: synthetic hair binding peptide derivative

<400> SEQUENCE: 97

Cys Asn Thr Pro Lys Glu Asn Trp Cys
1               5

<210> SEQ ID NO 98
<211> LENGTH: 9
<212> TYPE: PRT
<213> ORGANISM: Artificial Sequence
<220> FEATURE:
<223> OTHER INFORMATION: synthetic hair binding peptide derivative

<400> SEQUENCE: 98

Cys Asn Thr Pro Ala Ser Asn Arg Cys
1               5

<210> SEQ ID NO 99
<211> LENGTH: 9
<212> TYPE: PRT
<213> ORGANISM: Artificial Sequence
<220> FEATURE:
<223> OTHER INFORMATION: synthetic hair binding peptide derivative

<400> SEQUENCE: 99

Cys Pro Arg Gly Met Leu Ser Thr Cys
1               5

```
<210> SEQ ID NO 100
<211> LENGTH: 9
<212> TYPE: PRT
<213> ORGANISM: Artificial Sequence
<220> FEATURE:
<223> OTHER INFORMATION: synthetic hair binding peptide derivative

<400> SEQUENCE: 100

Cys Pro Pro Thr Tyr Leu Ser Thr Cys
 1               5

<210> SEQ ID NO 101
<211> LENGTH: 9
<212> TYPE: PRT
<213> ORGANISM: Artificial Sequence
<220> FEATURE:
<223> OTHER INFORMATION: synthetic hair binding peptide derivative

<400> SEQUENCE: 101

Cys Thr Pro Pro Thr His Arg Leu Cys
 1               5

<210> SEQ ID NO 102
<211> LENGTH: 9
<212> TYPE: PRT
<213> ORGANISM: Artificial Sequence
<220> FEATURE:
<223> OTHER INFORMATION: synthetic hair binding peptide derivative

<400> SEQUENCE: 102

Cys Leu Pro Thr Met Ser Thr Pro Cys
 1               5

<210> SEQ ID NO 103
<211> LENGTH: 9
<212> TYPE: PRT
<213> ORGANISM: Artificial Sequence
<220> FEATURE:
<223> OTHER INFORMATION: synthetic hair binding peptide derivative

<400> SEQUENCE: 103

Cys Leu Gly Thr Asn Ser Thr Pro Cys
 1               5

<210> SEQ ID NO 104
<211> LENGTH: 9
<212> TYPE: PRT
<213> ORGANISM: Artificial Sequence
<220> FEATURE:
<223> OTHER INFORMATION: synthetic hair binding peptide derivative

<400> SEQUENCE: 104

Cys Thr Pro Leu Thr Lys Glu Thr Cys
 1               5

<210> SEQ ID NO 105
<211> LENGTH: 9
<212> TYPE: PRT
<213> ORGANISM: Artificial Sequence
<220> FEATURE:
<223> OTHER INFORMATION: synthetic hair binding peptide derivative

<400> SEQUENCE: 105

Cys Thr Gln Pro His Asn Pro Pro Cys
 1               5

<210> SEQ ID NO 106
```

```
<211> LENGTH: 9
<212> TYPE: PRT
<213> ORGANISM: Artificial Sequence
<220> FEATURE:
<223> OTHER INFORMATION: synthetic hair binding peptide derivative

<400> SEQUENCE: 106

Cys Ser Leu Leu Ser Ser His Ala Cys
1               5

<210> SEQ ID NO 107
<211> LENGTH: 9
<212> TYPE: PRT
<213> ORGANISM: Artificial Sequence
<220> FEATURE:
<223> OTHER INFORMATION: synthetic hair binding peptide derivative

<400> SEQUENCE: 107

Cys Asn Ala Ser Pro Ser Ser Leu Cys
1               5

<210> SEQ ID NO 108
<211> LENGTH: 9
<212> TYPE: PRT
<213> ORGANISM: Artificial Sequence
<220> FEATURE:
<223> OTHER INFORMATION: synthetic hair binding peptide derivative

<400> SEQUENCE: 108

Cys His Ser Pro Ser Ser Leu Arg Cys
1               5

<210> SEQ ID NO 109
<211> LENGTH: 9
<212> TYPE: PRT
<213> ORGANISM: Artificial Sequence
<220> FEATURE:
<223> OTHER INFORMATION: synthetic hair binding peptide derivative

<400> SEQUENCE: 109

Cys Leu Glu Ser Thr Ser Leu Leu Cys
1               5

<210> SEQ ID NO 110
<211> LENGTH: 4
<212> TYPE: PRT
<213> ORGANISM: Artificial Sequence
<220> FEATURE:
<223> OTHER INFORMATION: synthetic linker

<400> SEQUENCE: 110

Gly Gly Gly Lys
1

<210> SEQ ID NO 111
<211> LENGTH: 5
<212> TYPE: PRT
<213> ORGANISM: Artificial Sequence
<220> FEATURE:
<223> OTHER INFORMATION: synthetic linker

<400> SEQUENCE: 111

Gly Gly His Gly Gly
1               5
```

SKIN OR HAIR BINDING PEPTIDES

BACKGROUND OF THE INVENTION

Various methods may be used for the selection and identification of compounds capable of binding specifically to a target in the presence of undesired background targets (anti-targets) using libraries of similar compounds. This invention is directed to peptides that bind specifically to a target such as skin or hair in the presence of an anti-target. The anti-target is hair when the target is skin and the anti-target is skin when the target is hair.

The literature is replete with examples of recent advances in methods for screening large library pools of compounds, especially peptides. Methods for screening these compounds to identify molecules that bind to a preselected target have also been advanced. One well-known method is biopanning which was originally developed by Smith, G. P., (1985), *Science* 228:1315. Biopanning in its simplest form is an in vitro selection process in which a library of phage-displayed peptides is incubated with a target. The target and phage are allowed to bind and unbound phage are washed away. The specifically bound phage are then acid eluted. The eluted pool of phage is amplified in vivo and the process is repeated. After a number of rounds individual clones are isolated and sequenced.

A number of variations of the biopanning technique first introduced by Smith have been described, and reference is made to Christian et al., (1992) *J. Mol. Biol.*, 227:711; Cwirla et al., (1990) *Proc. Natl. Acad. Sci. USA*, 87:6378; Cull et al., (1992) *Proc. Natl. Acad. Sci. USA*, 89:1865; Huls et al., (1996) *Nature Biotechnol.*, 7:276; and Bartoli et al., (1998) *Nature Biotechnol.*, 16:1068.

Huls et al., 1996 supra, describe a method comprising flow cytometry-based subtractive selection of phage antibody on intact tumor cells. The phage-displayed antibodies remain bound to the target during the flow-cytometric selection. However, prior to amplification the cell-bound phages are eluted from the target. WO 98/54312 discloses selection of antibodies under mild conditions with high affinities for antigens using antibody libraries displayed on ribosomes.

Balass et al., (1996) *Anal. Biochem.*, 243:264, describe the selection of high-affinity phage-peptides from phage-peptide libraries using a biotinylated target immobilized on a nitrostreptavidin matrix. Other selection methods include, for example, SELEX (U.S. Pat. No. 5,475,096) and selective targeting which includes deselection as disclosed in WO 01/79479.

SUMMARY OF THE INVENTION

In a first aspect the invention concerns a peptide which binds to skin but not to hair, and in a second aspect the invention concerns a peptide which binds to hair but not to skin.

In a third aspect the invention concerns a skin binding peptide including (a) any one of SEQ ID NOs. 1-24 or (b) an amino acid sequence having at least 50% sequence identity to any one sequence of SEQ ID NOs. 1-24 and including a sequence cluster selected from the group consisting of APQQRPMXTXXX (SEQ ID NO. 25); PPWXXXL (SEQ ID NO. 26); XXTXLTS (SEQ ID NO. 27); XPPLLXL (SEQ ID NO. 28); SXPSGAX (SEQ ID NO. 29); XQATFXX-NXXXX (SEQ ID NO. 30); VXTSQLXXXXXX (SEQ ID NO. 31); LXXXRMK (SEQ ID NO. 32), and HXXXYLT (SEQ ID NO. 33), wherein X represents any L-amino acid.

In one embodiment a skin binding peptide of the invention includes a C—C derivative. Particularly preferred skin binding peptides of the invention include a peptide having the amino acid sequence of SEQ ID NO. 1; a peptide including the sequence cluster of sequence XQATFXXNXXXX (SEQ ID NO. 30); a peptide having the amino acid sequence of SEQ ID NO. 5; a peptide having the sequence cluster of sequence LXXXRMK (SEQ ID NO. 32) and a peptide having the sequence cluster of APQQRPMXTXXX (SEQ ID NO. 25). In another embodiment the invention concerns a composition comprising one or more skin binding peptides as disclosed herein.

In a fourth aspect the invention concerns a hair binding peptide including (a) any one of SEQ ID NOs. 34-56 or (b) an amino acid sequence having at least 50% sequence identity to any one sequence of SEQ ID NOs. 34-56 and including a sequence cluster selected from the group consisting of NTPXXNX (SEQ ID NO. 57); PXXXLST (SEQ ID NO. 58); TXPTHR (SEQ ID NO. 59); LXTXSTP (SEQ ID NO. 60); and TPLTXXT (SEQ ID NO. 61) and XQXHNPP (SEQ ID NO. 62), wherein X represents any L-amino acid.

In one embodiment a hair binding peptide of the invention includes a C—C derivative. In another embodiment the invention concerns a composition comprising one or more hair binding peptides as disclosed herein.

DETAILED DESCRIPTION OF THE INVENTION

Figure 1:
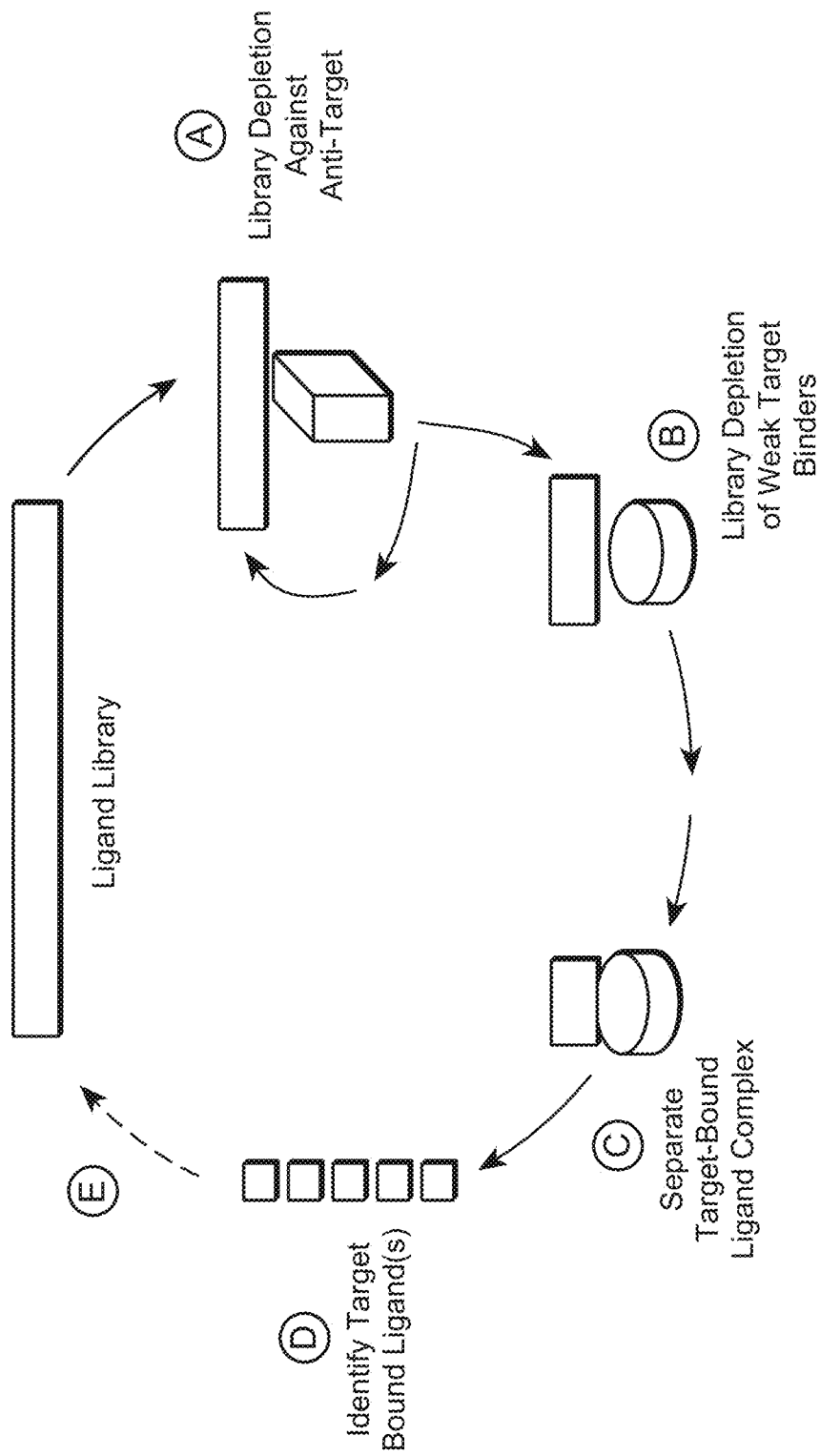
FIG. 1 is a general schematic diagram of a targeting method which maybe used to select for the skin or hair binding peptides identified herein. The method comprises the steps of, a) selection against anti-targets which provides a library of ligands depleted of anti-target bound ligands, b) selection for the target by formation of a target-bound ligand complex, c) separation of the target-bound ligand complex, d) identification of the target-bound ligands, and e) optionally sequencing the target-bound ligands, exposing the target-bound ligands to additional rounds of selective targeting, and/or diversification.

Unless defined otherwise, all technical and scientific terms used herein have the same meaning as commonly understood by one of ordinary skill in the art to which this invention pertains. For the purposes of the present invention, the following terms are used to describe the invention herein.

The term "ligand" refers to a molecule or compound that is recognized by a particular target or anti-target. The term is independent of molecular size or compositional feature. The ligand may serve as a substrate for an enzyme-catalyzed reaction, as an agonist, as an antagonist, act as a signal messenger, or stimulate or inhibit metabolic pathways. Ligands may be nucleic acids, peptides, peptide derivatives, peptidomimetics, polypeptides, small organic molecules, carbohydrates and other molecules that are isolated from a candidate mixture that acts on a target in a desirable manner. Preferably the desirable manner is binding the target.

The term "library" refers to a collection of chemical or biological entities that can be created in a single reservoir and simultaneously screened for a desired property. As used herein a library can have a minimum size of at least two members and may contain as many as $10^{15}$ members. In one aspect, the library has at least $10^2$ members. In another aspect, the library has at least $10^3$ members. In yet another aspect, the library has at least $10^6$ members. In a further aspect, the library has at least $10^9$ members. The size of a library refers to the total number of entities comprising the library whether the members are the same or different.

A "peptide library" refers to a set of peptides and to the peptides and any fusion proteins containing those peptides. Stochastic or random processes may be used to construct random peptides. The term "random" does not mean that the library composition is not known.

The term "peptide" refers to an oligomer in which the monomeric units are amino acids (typically, but not limited to L-amino acids) linked by an amide bond. Peptides may be two or more amino acids in length. Peptides identified according to the invention are preferably less than 50 amino acids in length, more preferably less than 30 amino acids in length, also preferably less than 25 amino acids in length, and preferably less than 20 amino acids in length. In one embodiment the identified binding peptides are between 4 and 20 and also between 6 and 15 amino acids in length. However, in general peptides may be up to 100 amino acids in length. Peptides that are longer than 100 amino acids in length are generally referred to as polypeptides. Standard abbreviations for amino acids are used herein. (See Singleton et al., (1987) *Dictionary of Microbiology and Molecular Biology*, Second Ed., page 35, incorporated herein by reference). The term "protein" is well known and refers to a large polypeptide.

A "binding peptide" according to the invention is a peptide that binds to a target (skin or hair) with a binding affinity of at least about $10^{-2}$M, at least about $10^{-3}$M, at least about $10^{-4}$ M, at least about $10^{-5}$ M, at least about $10^{-7}$M, at least about $10^{-9}$M, and preferably between about $10^{-2}$ M to $10^{-15}$ M, between about $10^{-2}$M to $10^{-10}$M and between $10^{-3}$ to $10^{-9}$M.

The term "nucleic acid" means DNA, RNA, single-stranded or double-stranded and chemical modifications thereof. Modifications may include but are not limited to modified bases, backbone modifications, methylations, unusual base pairing modifications, and capping modifications.

It will be appreciated by those skilled in the art that as a result of the degeneracy of the genetic code, a multitude of peptide encoding nucleotide sequences may be produced. "Percent sequence identity" with respect to a peptide or nucleic acid sequence refers to the percent of residues or codons that are identical in two sequences. Peptide or polynucleotides according to the invention may have at least 50%, at least 60%, at least 65%, at least 70%, at least 75%, at least 80%, at least 85%, at least 90% and at least 95% sequence identity to a reference sequence when optimally aligned. Optimal alignment of the sequences may be conducted by various known methods and computerized implementation of known algorithms (e.g. BLAST, TFASTA, BESTFIT, such as in the Wisconsin Genetics Software Package, Release 7.0, Genetics Computer Group, Madison, Wis.).

The term "target" or "anti-target" refers to molecules or heterogeneous molecules that have a binding affinity as defined herein, for a given ligand. Both target and anti-targets may be naturally occurring or synthetic molecules or heterogeneous molecules. In a preferred embodiment the target is skin or hair. Further when the target is skin, the anti-target is hair and when the target is hair, the anti-target is skin.

The binding affinity of a ligand for its target or anti-target may be described by the dissociation constant ($K_D$), concentration needed for 50% effective binding ($EC_{50}$), or concentration needed for 50% inhibition of binding of another compound that binds to the target ($IC_{50}$). $K_D$ is defined by $k_{off}/k_{on}$.

The $k_{off}$ value defines the rate at which the target-ligand complex breaks apart or separates. This term is sometimes referred to in the art as the kinetic stability of the target-ligand complex or the ratio of any other measurable quantity that reflects the ratio of binding affinities, such as an enzyme-linked immunosorbent assay (ELISA) signal or radio-active label signal.

"Selectivity" is defined by the ratio of binding affinities or $k_{off}$ for dissociation of the ligand-complex (target $K_D$/anti-target $K_D$). The $k_{on}$ value describes the rate at which the target and ligand combine to form the target-ligand complex.

The term "contacting" is broadly defined to mean placing a library of ligands and a target or anti-target in immediate proximity or association and includes in vitro and in vivo contact. The term includes touching, associating, joining, combining, intravenous injection, oral administration, intraperitoneally, topical application, intramuscular, inhalation, subcutaneous application and the like.

The term "separating" as used herein means to select, segregate, partition, isolate, collect, keep apart and disunite. Separation methods are well known to those in the art. These methods include affinity chromatography, washing, liquid transfer, centrifugation, high-performance liquid chromatography (HPLC), filtration, such as gel filtration, enzyme-linked immunosorbent assays (ELISA), and fluorescence-activator cell sorting (FACS). The choice of a separation method is well within the skill of one in the art, and a variety of instruments used for these separation methods are commercially available. (See Kenny and Fowell (eds) (1992) *Practical Protein Chromatography Methods in Molecular Biology*, vol. 11, Humana Press, Totowa N.J.).

"Amplifying" means a process or combination of process steps that increases the amount or number of copies of a molecule or class of molecules. In one aspect, amplification refers to the production of additional copies of nucleic acid sequences that is carried out using polymerase chain reaction (PCR) technology well known in the art.

As used in the specification, the singular "a", "an" and "the" include the plural references unless the context clearly dictates otherwise. For example, the term "a ligand" may include a plurality of ligands.

The following references describe the general techniques employed herein: Sambrook et al., (1989) *Molecular Cloning: A Laboratory Manual*, Cold Spring Harbor Laboratory Press, Cold Spring Harbor, N.Y.; Innis et al., *PCR Protocols—A Guide to Methods and Applications* (1990), Academic Press, Inc.; Kay et al., (1996) *Phage Display of Peptides and Proteins*, Academic Press; Ausubel et al., (1987) *Current Protocols in Molecular Biology*, Greene-Publishing & Wiley Interscience NY (Supplemented through 1999); Berger and Kimmel, (1987) *Methods in Enzymology*, Vol. 152. Academic Press Inc., San Diego, Calif.

The skin or hair binding peptides of the invention may be obtained and identified using methods well known in the art. These methods may include use of random peptide libraries, synthetic peptide libraries, peptide loop libraries, antibody libraries and protein libraries. These libraries as well as methods for making the libraries are well known. Reference is made to Barbas, C. F. (1993) *Current Opinion in Biotech.*, 4:526; Cwirla et al., (1990) supra; Scott and Smith, (1990) *Science*, 249:386; Cull et al., (1992) supra; Pinilla et al., (1994) *Biochem. J.* 301:847; Sambrook et al., (1989) supra; Ausubel et al., (1987) supra; and Gubler and Hoffman, (1983) *Gene* 25:263; U.S. Pat. No. 5,283,173; U.S. Pat. No. 5,270,181; U.S. Pat. No. 5,292,646; U.S. Pat. No. 5,605,793; U.S. Pat. No. 5,733,731; Stemmer (1994), *Proc. Natl. Aca. Sci.*

USA 91:10747; WO 97/22617; Foder et al., (1991) *Science* 251:767; Lam et al., (1993) *Bioorg. Med. Chem. Lett.*, 3:419; Tjoeng et al., (1990) *Int. J. Pept. Protein Res.* 35:141; and WO96/33010.

Various companies now make instrumentation to generate combinatorial libraries from both solution and solid phase synthesis (CombiChem Inc. (San Diego, Calif.); Advanced ChemTech (Louisville); Zymark Corp. (MA); and Hewlett Packard (CA)).

Not only are standard methods for generating libraries of ligands well known, but also ligand libraries may be obtained commercially, for example from Sigma (St. Louis Mo.) or from various public sources such as American Type Culture Collection (ATCC) and the National Institute of Health (NIH).

Screening techniques may include yeast display, ribosome display, biopanning and acid elution. One general method for screening a library of ligands having a binding affinity and selectivity for a selected target includes preparing or obtaining a library of ligands, preferably peptides of different sequences and more preferably a random peptide library. Deselecting ligands that bind with an anti-target by contacting the ligand library with an anti-target under conditions favorable for binding between the ligands of the library and the anti-target; allowing the anti-target to bind with the ligands; and separating the anti-target non-binders (unbound ligands) from the anti-target ligand bound molecules and any free ligands. Contacting the anti-target non-binders with a selected target under suitable conditions and allowing them to bind. Ligands with an affinity for the target will bind to form a target-bound ligand complex. The removal of ligands bound to the anti-target and removal of weak target-bound ligands may generally be referred to as library depletion. The target-bound ligand complex is then separated from the remaining mixture including the unbound ligands. The target-bound ligand complex or the target-bound ligands may optionally be subjected to further rounds of selection (FIG. 1).

Once selected, a binding peptide may be sequenced, amplified or produced in bulk by any one of a number of standard techniques. Some of these techniques include polymerase chain reaction (PCR), direct amino acid sequencing of the selected peptide by using peptide sequencers, mass spectrophotometry (MS), surface plasmon resonance, immunoprecipitation and nuclear magnetic resonance (NMR) spectroscopy. Reference is made to U.S. Pat. No. 4,683,202; Szabo et al., (1995) *Curr. Opin. Struct. Bio.* 5:699; Harlow et al., (1999) *Using Antibodies, A Laboratory Manual*, Cold Spring Harbor Press; Hajduk et al., (1999) *J. Med Chem.*, 42:2315; Cao et al., (1997) *Techniques in Protein Chemistry VIII*, Academic Press pages 177-184; Youngquist et al., (1995) *J. Am. Chem. Soc.* 117:3900; Cheng et al., (1995) *J. Am. Chem. Soc.*, 117:8859; Walk et al., (1999) *Angew. Che. Int. Ed.*, 38:1763; Wu et al., (1997) in *Chemistry and Biology*, vol. 14(9):653; Marshall et al., (1998), *Mass Spectrometry Reviews* 17:1; and Nelson et al., (1999) *J. Mol. Recognition*, 12:77.

The binding peptides may be produced recombinantly using genetic engineering or the peptide may be chemically synthesized.

In one embodiment, the peptide binding affinity for the target according to the present invention for $K_D$, $EC_{50}$ or $IC_{50}$ is in the range of between about $10^{-7}$M to $10^{-15}$M, although higher or low binding affinities may be achieved. In one aspect, the binding affinity is in the range of at least about $10^{-2}$M, at least about $10^{-3}$M, at least about $10^{-4}$M, at least about $10^{-5}$M, at least about $10^{-7}$M, at least about $10^{-9}$M and also at least about $10^{-12}$M. In another embodiment, the affinity is less than about $10^{-7}$M. In another aspect, $k_{off}$ values for the ligand-target complex will be less than about $10^{-2}$ sec$^{-1}$, less than about $10^{-3}$ sec$^{-1}$, less than about $10^{-4}$ sec$^{-1}$, and also less than about $10^{-5}$ sec$^{-1}$. The binding peptides of the invention will not bind with any significance to the anti-target. While not meant to limit the invention, a preferred binding ligand may have a $K_D$ for the anti-target greater than about $10^{-4}$ M, and preferably greater than about $10^{-1}$ M.

The binding peptides according to the invention may be characterized not only by the binding affinity of the ligand to a target, but also may be characterized by the selectivity of the ligand-target complex. The selectivity of ligand binding for a target compared to ligand binding to an anti-target can be defined by a ratio of $K_D$, $EC_{50}$ or $IC_{50}$ in the range of about 1.5:1 to 500:1. In one aspect, selectivity is at least about 2:1, at least about 3:1, at least about 5:1, at least about 10:1, at least about 20:1, at least about 30:1, at least about 50:1, and at least about 100:1.

Methods for measuring binding affinities and selectivity are well known in the art, and these methods include but are not limited to measurement by radio-labeled release and competition assay; by isothermal titration calorimetry; biosensor binding assays (Morton & Myszka, (1998) *Methods Enzymol.* 295:268-294); by fluorescence and chemiluminescence spectroscopy; and by mass spectrophotometry (Gao et al., (1996), *J. Med, Chem.*, 39:1949).

In one embodiment, preferred skin binding peptides according to the invention are listed in Table 1.

TABLE 1

| Skin binding peptides | |
|---|---|
| KQATFPPNPTAY | SEQ ID NO. 1 |
| QATFMYN | SEQ ID NO. 2 |
| HGHMVSTSQLSI | SEQ ID NO. 3 |
| VLTSQLPNHSM | SEQ ID NO. 4 |
| LSPSRMK | SEQ ID NO. 5 |
| LPIPRMK | SEQ ID NO. 6 |
| HSTAYLT | SEQ ID NO. 7 |
| HQRPYLT | SEQ ID NO. 8 |
| APQQRPMKTFNT | SEQ ID NO. 9 |
| APQQRPMKTVQY | SEQ ID NO. 10 |
| PPWLDLL | SEQ ID NO. 11 |
| PPWTFPL | SEQ ID NO. 12 |
| SVTHLTS | SEQ ID NO. 13 |
| VITRLTS | SEQ ID NO. 14 |
| FPPLLRL | SEQ ID NO. 15 |
| DLKPPLLALSKV | SEQ ID NO. 16 |
| SHPSGALQEGTF | SEQ ID NO. 17 |
| FPLTSKPSGACT | SEQ ID NO. 18 |
| DLKPPLLALSKV | SEQ ID NO. 19 |
| PLLALHS | SEQ ID NO. 20 |
| YPISTQI | SEQ ID NO. 21 |
| YAKQHYPISTFK | SEQ ID NO. 22 |

TABLE 1-continued

Skin binding peptides

| HSTAYLT | SEQ ID NO. 23 |
| STAYLVAMSAAP | SEQ ID NO. 24 |

Particularly preferred embodiments include skin binding peptides having an amino acid sequence of SEQ ID NO. 1, SEQ ID NO. 3, SEQ ID NO. 5, SEQ ID NO. 6, SEQ ID NO. 8 and SEQ ID NO. 15, and particularly SEQ ID NO. 1 and SEQ ID NO. 5.

In another embodiment, skin binding peptides of the invention have repeatable motifs. A repeatable motif is defined as including at least three consecutive amino acid residues in a peptide string and may include four, five, six, seven, eight or nine consecutive amino acids residues wherein the repeatable motif is found in at least two of the peptides listed in Table 1 or at least two of the peptides listed in Table 2. Preferred repeatable motifs for skin binding peptides include QATF, TSQL, RMK, YLT, APQQRPM, PMKT, PPW, LTS, PPLL, APQQRMKT, PSGA, PLLAL, STAYL, and YPIST.

In yet a further embodiment, skin binding and hair binding peptides of the invention include sequence clusters. A sequence cluster includes a repeatable motif as defined herein and 1 or 2 amino acid residues identical to amino acid residues found in the binding peptides listed in Table 1 or Table 2 when the same repeatable motif in each peptide is aligned and further including 1 to 8, preferably 1 to 3 intervening amino acid residues located either before or after the repeatable motif.

Preferred sequence clusters for skin binding peptides include the following:

| APQQRPMXTXXX | SEQ ID NO. 25 |
| PPWXXXL | SEQ ID NO. 26 |
| XXTXLTS | SEQ ID NO. 27 |
| XPPLLXL | SEQ ID NO. 28 |
| SXPSGAX | SEQ ID NO. 29 |
| XQATFXXNXXXX | SEQ ID NO. 30 |
| VXTSQLXXXXXX | SEQ ID NO. 31 |
| LXXXRMK | SEQ ID NO. 32 |
| HXXXYLT | SEQ ID NO. 33 |

X represents any L-amino acid. Particularly preferred skin binding peptides are peptides having the sequence cluster of APQQRPMXTXXX (SEQ ID NO. 25), the sequence cluster of XQATFXXNXXXX (SEQ ID NO. 30) or LXXXRMK (SEQ ID NO. 32).

In a further embodiment, preferred hair binding peptides according to the invention are listed in Table 2.

TABLE 2

Hair binding peptides

| NTPKENW | SEQ ID NO. 34 |
| NTPASNR | SEQ ID NO. 35 |
| PRGMLST | SEQ ID NO. 36 |

TABLE 2-continued

Hair binding peptides

| PPTYLST | SEQ ID NO. 37 |
| TIPTHRQHDYRS | SEQ ID NO. 38 |
| TPPTHRL | SEQ ID NO. 39 |
| LPTMSTP | SEQ ID NO. 40 |
| LGTNSTP | SEQ ID NO. 41 |
| TPLTGSTNLLSS | SEQ ID NO. 42 |
| TPLTKET | SEQ ID NO. 43 |
| KQSHNPP | SEQ ID NO. 44 |
| QQSHNPP | SEQ ID NO. 45 |
| TQPHNPP | SEQ ID NO. 46 |
| STNLLRTSTVHP | SEQ ID NO. 47 |
| HTQPSYSSTNLF | SEQ ID NO. 48 |
| SLLSSHA | SEQ ID NO. 49 |
| QQSSISLSSHAV | SEQ ID NO. 50 |
| NASPSSL | SEQ ID NO. 51 |
| HSPSSLR | SEQ ID NO. 52 |
| K H/R/N SHHTH | SEQ ID NO. 53 |
| E H/R/N SHHTH | SEQ ID NO. 54 |
| SHHTHYGQPGPV | SEQ ID NO. 55 |
| LESTSLL | SEQ ID NO. 56 |

The binding peptides identified as SEQ ID NO: 53 and SEQ ID NO. 54 may include histidine (H), arginine (R) or asparagine (N) as the second amino acid in the peptide string.

In another embodiment, hair binding peptides of Table 2 have repeatable motifs. Preferred repeatable motifs for hair binding peptides include STNL, LSSHA, SPSSL, SHHTH, NTP, LST, PTHR, STP, TPLT and HNPP.

In yet a further embodiment hair binding peptides of the invention include sequence clusters. Preferred sequence clusters for hair binding peptides include the following:

| NTPXXNX | SEQ ID NO. 57 |
| PXXXLST | SEQ ID NO. 58 |
| TXPTHRX | SEQ ID NO. 59 |
| LXTXSTP | SEQ ID NO. 60 |
| TPLTXXT | SEQ ID NO. 61 |
| XQXHNPP | SEQ ID NO. 62 |

X represents any L amino acid.

In a further embodiment a binding peptide according to the invention includes peptides having a sequence cluster or repeatable motif as disclosed above, wherein the peptide has at least 50%, at least 55%, at least 60%, at least 65%, at least 70%, at least 75%, at least 80%, and at least 85% amino acid sequence identity with a reference binding peptide of Table 1 or Table 2. The peptide, which includes a sequence cluster or repeatable motif, will also have a binding affinity for the same target as the reference peptide in the range of $10^{-2}$ to $10^{-15}$M, at least about $10^{-2}$M, at least about $10^{-3}$M, at least about $10^{-5}$M, at least about $10^{-7}$M, and at least about $10^{-5}$M. Preferably the binding affinity will be essentially the same or greater than the binding affinity of the reference binding peptide.

Additionally a skin or hair binding peptide according to the invention may include a cysteine (C) residue on either or both ends of the peptide. These peptides are more specifically referred to herein as C—C derivatives. Nonlimiting examples of C—C derivative skin binding peptides include C-SEQ ID NO. 2-C; C-SEQ ID NO. 5-C; C-SEQ ID NO. 6-C; C-SEQ ID NO. 7-C; C-SEQ ID NO. 8-C; C-SEQ ID NO. 11-C; C-SEQ ID NO. 12-C; C-SEQ ID NO. 13-C; C-SEQ ID NO. 14-C; C-SEQ ID NO. 15-C; C-SEQ ID NO. 20-C; C-SEQ ID NO. 21-C; and C-SEQ ID NO. 23-C. Nonlimiting examples of C—C derivative hair binding peptides include C-SEQ ID NO. 34-C; C-SEQ ID NO. 35-C; C-SEQ ID NO. 36-C; C-SEQ ID NO. 37-C; C-SEQ ID NO. 39-C; C-SEQ ID NO. 40-C; C-SEQ ID NO. 41-C; C-SEQ ID NO. 43-C; C-SEQ ID NO. 46-C; C-SEQ ID NO. 49-C; C-SEQ ID NO. 51-C; C-SEQ ID NO. 52-C; and C-SEQ ID NO. 56-C. A binding peptide which comprises a sequence cluster may also include a cysteine residue on either or both ends of the peptide.

A linker molecule (also sometimes referred to in the art as a spacer moiety) may be added to either end of a binding peptide according to the invention. A linker molecule may be any carbon containing molecule such as, a short peptide, for example GGH, GGGK, and GGHGG; a carbon chain, for example $(CH_2)n$ wherein n equals 1 to 10; a polymer, for example $PEG(CH_2—O)n$ wherein n equals 2-20; a sugar; a lipid or the like.

In one application, skin or hair binding peptides of the invention may be used in compositions for personal care applications. These compositions may take the form of lotions, creams, gels, sprays, shampoos and conditioners and the like.

Non-limiting examples of personal care applications which include a binding peptide of the invention are the following: a) using a skin binding peptide with an emollient which may result in the enhancement of the moisturizing properties of the emollient; b) combining a skin binding peptide with a bleaching or tanning agent which may result in the enhancement of skin bleaching or tanning properties; c) combining a skin binding peptides with a sunscreen for topical application; and d) combining a hair binding peptide with a dye or oxidizing agent wherein the hair coloring properties of the hair coloring formulation may be enhanced.

One skilled in the art is aware of various references including lists of cosmetic raw materials which may be used in personal care compositions. Two such references are *CTFA International Buyers' Guide,* 2002, Cosmetic, Toiletry and Fragrance Association, Washington D.C. and *CTFA International Cosmetic Ingredient Dictionary and Handbook,* 7th Ed. (1997) Vol. 2, Eds. Wenninger and McEwen, Cosmetic, Toiletry and Fragrance Association, Washington D.C. Also reference is made to WO 00/24372; WO 96/16630 and Sagarin, *Cosmetics, Science and Technology,* 2nd Ed. Vol. 1 (1972).

Accordingly, the following examples are offered by way of illustration, and are not meant to limit the invention in any manner. Those skilled in the art will recognize or be able to ascertain using no more than routine experimentation, many equivalents to the specific embodiments of the invention described herein.

The contents of all references, patents and published patent applications cited throughout this application are hereby incorporated by reference in their entirety.

EXPERIMENTAL

The procedures for restriction digest, ligation, preparation of competent cells using calcium chloride, preparation of 20 mg/ml isopropyl (IPTG), preparation of 20 mg/ml 5-bromo-4-chloro-3-indolyl-β-D-galactoside (X-gal), and preparation of phosphate-buffered saline (PBS) were according to well-known methods in the art and can be found in Sambrook et al. (1989) supra. Phage-displayed libraries (cyclic 7-mer, linear 7-mer and linear 12-mer) were supplied by New England Biolabs ((NEB; Beverly, Mass.). Restriction endonucleases EagI and Acc65I, 10× NEBuffer 3, T4 DNA ligase, alkaline calf intestinal phosphatase, *E. coli* ER2537 host strain, and M13KE gIII cloning vector were supplied by NEB and used according to the manufacturer's instructions unless stated otherwise. Taq polymerase, 10× PCR Buffer, and dNTP mix were supplied by Roche Molecular Biochemicals (Indianapolis, Ind.). The HotStart Taq Master Mix kit for PCR came from Qiagen (Valencia, Calif.). PCR was carried out using a HYBAID Omn-E Thermocycler from E&K Scientific Products (Campbell, Calif.) or PTC 2000 DNA Engine™ from M.J. Research Inc. (Roche Molecular Systems, Inc. Alameda, Calif.). Nondenaturing polyacrylamide gels (8%) and D-15 DNA markers were obtained from Novex (San Diego, Calif.) and 2% E-gels and TOPO cloning kits were obtained from Invitrogen (Carlsbad, Calif.). Both the QIAquick Gel Extraction Kit and QIAquick PCR Purification Kit were obtained from QIAGEN (Valencia, Calif.). AmpliWax™ PCR Gems were obtained from Perkin Elmer (Boston, Mass.).

Example 1

Screening for Peptides Selected to Target Human Skin and Not Hair

Two 3 inch strands of dark human hair (International Hair Importers & Products, White Plains, N.Y.) were placed in BSA blocked 50 ml conical tubes containing 10 ml of a 2% Neutrogena® Bath Gel (Neutrogena Corp.) solution in DI water. 10 μL of cyclic 7-mer or linear 12-mer peptide libraries ($10^{10}$ pfu/μl), or wild type phage ($10^9$ pfu/μl) were added and the samples mixed at room temperature for 15 min with rotatory shaking (30 rpm). The unbound supernatant was transferred to a new tube containing an additional two 3 inch strands of dark hair, and incubated at room temperature for 15 min with rotary shaking. After this second hair incubation, 500 μl of the solution was transferred to the surface of human skin tissues (EpiDerm™, MatTek Corp. Ashland, Mass.) in a 6 well culture plate containing 0.9 mL tissue culture media (MatTek Corp) for 30 minutes at room temperature with gentle agitation. The skin tissues were removed and washed 2× in 50 mls of 2% bath gel for 5 min each and 3× in 50 mls of PBS for 5 min each in blocked 50 mL conical tubes. After the final PBS wash, the skin tissues were frozen at −20° C. followed by PCR of the target bound ligand phage. Table 1 illustrates the target bound skin peptides screened according to this example.

Example 2

Screening for Peptides Selected to Target Human Hair and Not Skin

Pre-equilibrated skin tissues were placed into a 6 well culture plate containing fresh 0.9 mL tissue culture media and 300 µl of a 2% Neutrogena® Bath Gel containing, 10 µL of cyclic 7-mer or linear 12-mer peptide libraries ($10^{10}$ pfu/µl), or wild type phage ($10^9$ pfu/µl) were added to the skin surface. The samples were incubated at room temperature for 15 min with gentle agitation. The unbound supernatant was transferred to a new well containing skin tissue and the procedure was repeated. The incubation solution was transferred to nine 3 inch dark hair (International Hair Importers & Products, White Plains, N.Y.) strands in 50 ml tubes containing 10 ml of 2% body gel for 30 minutes at room temperature with rotatory shaking (30 rpm). The hair samples were then washed with 1×50 mls, 2×50 mls, or 4×50 mls of 2% bath gel; Wash cycles in PBS followed (1×25 mls for 5 min, 1×25 mls for 2 min, 2×50 mls for 5 min each, 150 mls total). After the final PBS wash, the hair samples containing bound phage peptides were frozen at −20° C. Table 2 illustrates target bound hair peptides screened according to this example.

Example 3

Selection of Phage-Peptides that Bind to Hair or Skin Using PCR for Identification of High Affinity Phage-Peptide Clones The skin swatches and hair samples were frozen at −20° C. until PCR. In one example, PCR was performed directly on the hair and skin samples using the following conditions in 0.5 ml PCR tubes with the following reagents:

50 µl reaction mix (HotStart)

2 µl CB05 primer (25 µM)

2 µl CB12 primer (25 µM)

46 µl sterile dH$_2$O

5 µl of BSA at 10 mg/ml and 50 µl of mineral oil were added. PCR amplification was performed post initiation at 95° C. for 15 min, using 30 cycles of denaturation at 94° C. for 30 sec, annealing at 58° C. for 30 sec and synthesis at 72° C. for 60 sec. Extension was preformed at 72° C. for 10 min. Primers were obtained from Operon Technologies, Inc. (Alameda, Calif.). The sequences of the primers were

```
                                           SEQ ID NO. 63
CB05   CGTAGTGGCATTACGTATTTTACCCGTTTAATGG (5'-3')

SEQ ID NO. 64
CB12   CGAGAGGGTTGATATAAGTATAGCCCGGAATAGG (5'-3')
```

Additionally 1 µl of the different PCR products was subjected to another round of PCR using the same program but the following ingredients were added:

50 µl reaction mix (HotStart)

1 µl CM13 01 primer (50 µM)

1 µl CM13 02 primer (50 µM)

47 µl sterile dH$_2$O

50 µl of BSA at 10 mg/ml and µl of mineral oil were added. Primers were obtained from Operon Technologies, Inc. (Alameda, Calif.). The sequences for the primers were

```
CM13 01
CCTCGAAAGCAAGCTGATAAACCG (5'-3')     SEQ ID NO. 65

CM13 02
CATTCCACAGACAACCCTCATAG (5'-3').     SEQ ID NO. 66
```

The PCR products were visualized on a 2% E-gel along with PCR products from dilutions of the various initial phage peptide libraries (positive control) and molecular weight markers, run under 65V for 40 min. 4 µl of the PCR products were subject to TOPO cloning and transformation according to standard protocol but all incubations were done for 30 minutes. The individual clones were submitted to PCR (12.5 µl Master Mix, 0.1 µl each of CM13 01 and CM13 02 primers, 12.3 µl sterile water per clone) using the same program as described above. Sequencing using 1 µl of PCR product and 11 µl of g96 primer was completed at Sequetech (Mountain View, Calif.); Biotech Core, Inc (Mountain View, Calif.) or internally using an ABI Applied Biosystem 373XL.

Example 4

Cloning of PCR Products

PCR products from the first round of selection were cloned as follows:

Vector Preparation:

10 µg of M13KE vector (New England Biolabs (NEB), Beverly, Mass.) was digested overnight (16 h) at 37° C. and according to NEB recommended conditions, digestion was performed in 400 µl total volume as follows: M13KE, 10 µl; Eag 1, 10 µl; Acc65 I, 10 µl; 10×NEB buffer 3, 40 µl; 100× BSA 4 µl; and dH$_2$O, 326 µl. The digested vector was purified using Qiagen PCR Purification Kit (Qiagen) using 30 µl of elution buffer (EB). The purified digest was stored at −20° C.

Insert Preparation:

PCR product from the first round of selection was purified using the Qiagen Purification Kit and eluted in 30 µl of EB buffer. 15 µl of the purified material was digested overnight in 100 µl total volume as follows: PCR product, 15 µl; Eag1, 1 µl; Acc651, 1 µl; 10×NEB buffer 3, 10 µl; 100×BSA, 1 µl; and dH$_2$O, 64 µl. The digestion was followed by a heat shock treatment at 60° C. for 20 min and the product was stored at −20° C. until further use.

The ligation was performed as described below using the Takara kit at 16° C. for 30 min, then placed on ice. Vector preparation, 1 µl; Insert preparation, 1 µl; EB buffer, 3 µl; and Solution 1, 5 µl from Takara BioInc., (Shiga, Japan).

Transformation:

5 µl of ligation mixture was used to transform 50 µl of TOP10F' chemically competent cells (Invitrogen) according to the commercial protocol. The cells were grown on LB plates overnight at 37° C.

The phage peptide libraries were amplified and titered according to standard techniques. Subsequent rounds of deselection and selection may also be performed according to the methods described above.

Example 5

Stability of Phage-Peptide Libraries in Shampoo and Bath Gel

Stability of the three phage display libraries (Ph.D.-7, Ph.D.-C7C and Ph.D.-12, New England Biolabs) was evaluated in a 2% solution of commercially available Neutrogena® Anti-Residue shampoo and in a 2% solution of Neutrogena® Bath Gel. 10 µL of each phage display library was added to 150 µL of either the shampoo or the bath gel solution in a micro titer plate (MTP). After 30 minutes, 60 minutes and 120 minutes, a 20 µL aliquot was removed from each well and serially diluted in 180 µL of LB broth. The diluted samples, containing the phage peptide libraries, from $10^6$ to $10^4$ PFU/mL, were added to 20 µL of 20 mg/mL isopropyl-β-D-thiogalactopyranoside (IPTG) and 200 µL of *E. coli* ER2537 cell culture in LB broth, mixed and incubated for 1 to 5 minutes. The infected cells were added to 3 mL of pre-heated (55° C.) LB agar tops containing 20 µL of 40 mg/mL X-gal (in DSMO), vortexed and immediately poured over pre-heated (37° C.) LA agar plates. Plates were cooled and incubated overnight at 37° C. The number of colonies on each plate were counted and the number of plaque forming units per mL (pfu/mL) were calculated for each plate.

pfu/mL=(# colonies/10 µL phage)×(dilution factor)×(1000 µL/1 mL)

Figure 2:
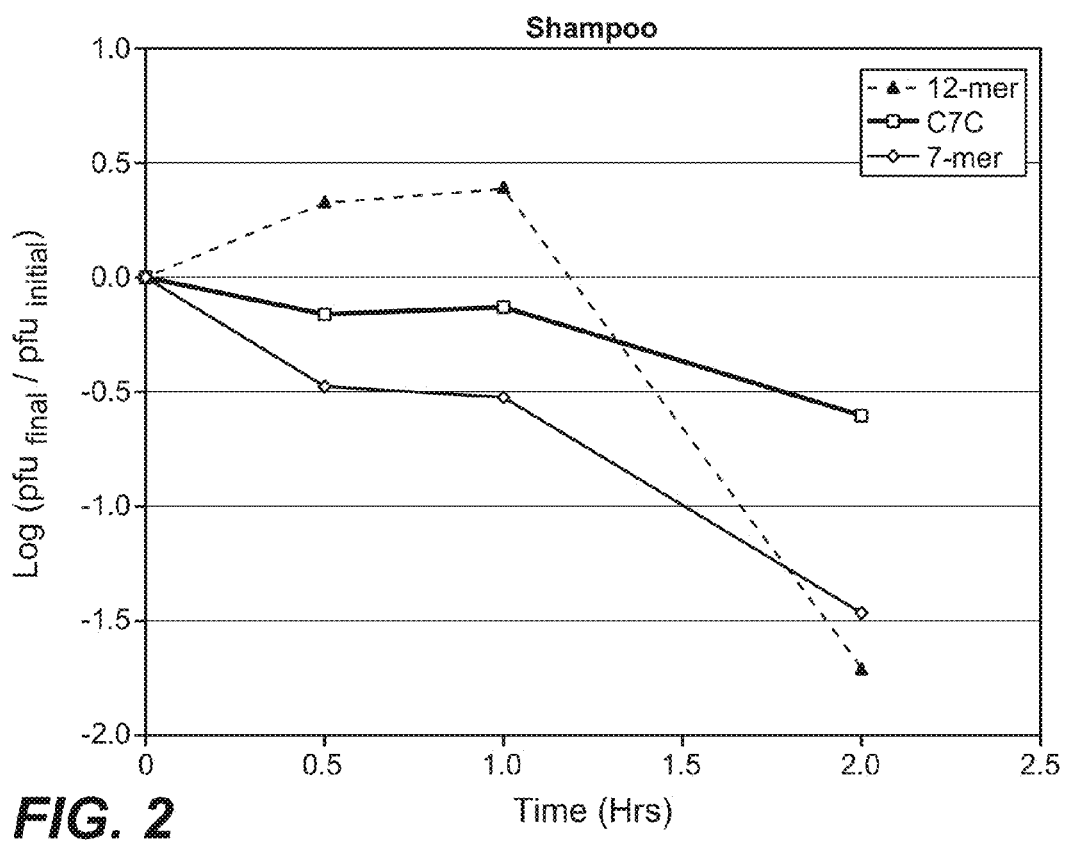
FIG. 2 illustrates the stability of phage-peptide libraries (Ph.D. 7, Ph.D. C7C and Ph.D.12) in Neutrogena® Shower Shampoo.
Figure 3:
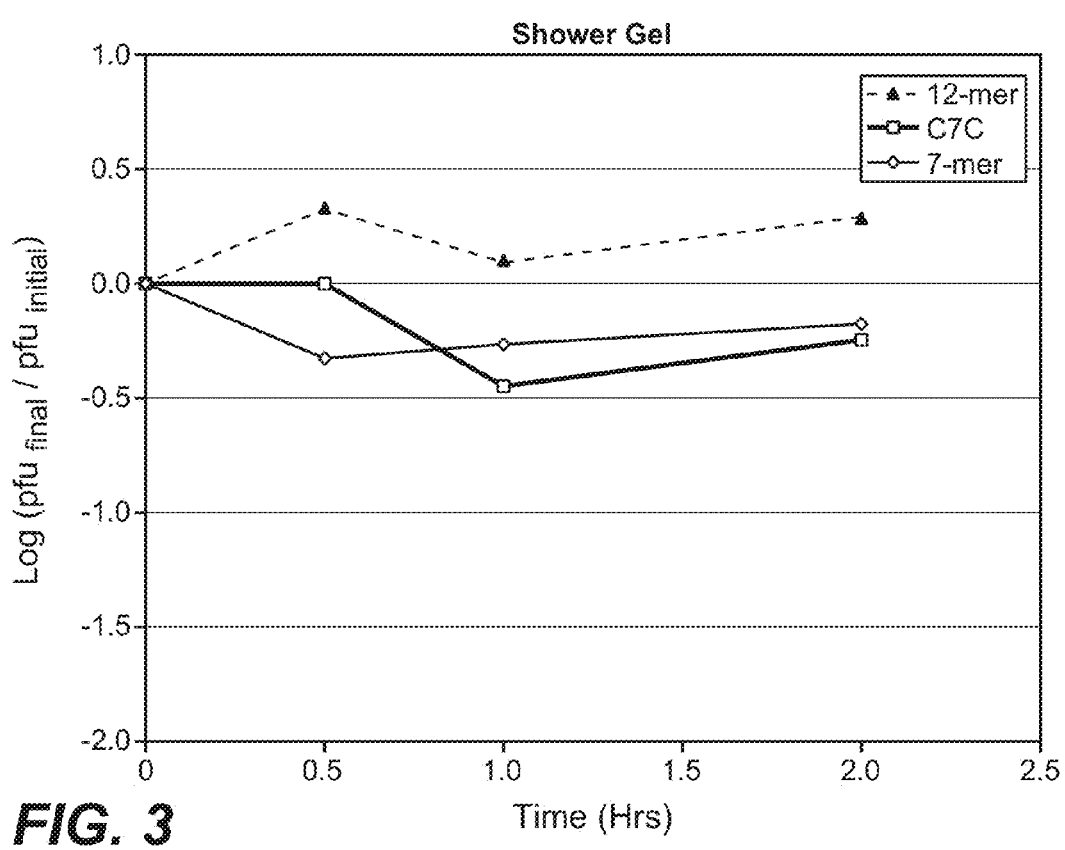
FIG. 3 illustrates the stability of phage-peptide libraries (Ph.D. 7, Ph.D. C7C and Ph.D.12) in Neutrogena® Bath Gel.

FIGS. 2 and 3 illustrate the stability of the phage populations in shampoo (FIG. 2) and shower gel (FIG. 3). The phage display libraries were more stable in the bath gel solution than in the shampoo solution. The pfu/mL of the phage libraries decreased by less than one log unit in the bath gel solution, but they decreased by up to two log units in the shampoo.

The invention claimed is:

1. An isolated hair binding peptide comprising the amino acid sequence of SEQ ID NO: 34.

2. The hair binding peptide according to claim 1, wherein the hair binding peptide consists of SEQ ID NO: 34.

3. A composition comprising the hair binding peptide of claim 1.

4. A composition comprising the hair binding peptide of claim 2.

* * * * *